United States Patent
Jeong (10) Patent No.: US 10,918,760 B2
(45) Date of Patent: Feb. 16, 2021

(54) DEODORIZATION MODULE AND STORAGE APPARATUS COMPRISING SAME

(71) Applicant: SEOUL VIOSYS CO., LTD., Ansan-si (KR)

(72) Inventor: Jae Hak Jeong, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 0 days.

(21) Appl. No.: 16/239,528

(22) Filed: Jan. 4, 2019

(65) Prior Publication Data

US 2019/0134251 A1  May 9, 2019

Related U.S. Application Data

(63) Continuation of application No. PCT/KR2017/006829, filed on Jun. 28, 2017.

(30) Foreign Application Priority Data

Jul. 5, 2016 (KR) .................. 10-2016-0084771

(51) Int. Cl.
| | | |
|---|---|---|
| *A61L 9/20* | (2006.01) | |
| *F25D 17/06* | (2006.01) | |
| *F25D 17/04* | (2006.01) | |
| *B01D 46/00* | (2006.01) | |

(52) U.S. Cl.
CPC .................. *A61L 9/205* (2013.01); *A61L 9/20* (2013.01); *B01D 46/0038* (2013.01);
(Continued)

(58) Field of Classification Search
CPC ........ A61L 9/205; A61L 9/20; A61L 2209/14; F25D 17/04; F25D 17/042; F25D 17/06;
(Continued)

(56) References Cited

U.S. PATENT DOCUMENTS

| | | |
|---|---|---|
| 5,078,971 A | 1/1992 | Matuda et al. |
| 10,143,769 B2 | 12/2018 | Park et al. |

(Continued)

FOREIGN PATENT DOCUMENTS

| | | |
|---|---|---|
| JP | 2004-000413 | 1/2004 |
| KR | 20-0348511 | 4/2004 |

(Continued)

OTHER PUBLICATIONS

International Search Report dated Oct. 12, 2017, issued in International Patent Application No. PCT/KR2017/006829.
(Continued)

*Primary Examiner* — Sean E Conley
*Assistant Examiner* — Brendan A Hensel
(74) *Attorney, Agent, or Firm* — H.C. Park & Associates, PLC (57) ABSTRACT

A deodorization module and a storage apparatus, the deodorization module including: a housing having one surface including a curved surface; a suction port formed on one surface of the housing to draw in external air; a fan disposed in the suction port and drawing in air; a discharge port formed on one surface of the housing to discharge the air drawn through the fan into the outside of the housing; a photocatalytic filter disposed between the fan and the discharge port and including a through hole through which air passes; and a light source module for irradiating ultraviolet rays onto the photocatalytic filter.

16 Claims, 8 Drawing Sheets

(52) U.S. Cl.
CPC ........... *F25D 17/04* (2013.01); *F25D 17/042* (2013.01); *F25D 17/06* (2013.01); *A61L 2209/14* (2013.01); *F25D 2317/0415* (2013.01); *F25D 2317/0417* (2013.01); *F25D 2317/0681* (2013.01)

(58) Field of Classification Search
CPC ..... F25D 2317/0681; F25D 2317/0417; F25D 2317/0415; B01D 46/0038
See application file for complete search history.

(56) References Cited

U.S. PATENT DOCUMENTS

| 2002/0094298 | A1* | 7/2002 | Monagan | A61L 9/20 422/5 |
| 2010/0293907 | A1* | 11/2010 | Zheng | B01D 46/0023 55/337 |
| 2012/0181911 | A1* | 7/2012 | Kim | A61L 2/14 312/405 |
| 2015/0033784 | A1* | 2/2015 | Park | F25D 11/00 62/264 |
| 2015/0064069 | A1* | 3/2015 | Yi | F24F 1/0071 422/121 |
| 2017/0036516 | A1* | 2/2017 | Kim | A61L 9/205 |

FOREIGN PATENT DOCUMENTS

| KR | 20-0410245 | 3/2006 |
| KR | 10-2015-0014815 | 2/2015 |
| KR | 10-1559324 | 10/2015 |

OTHER PUBLICATIONS

Supplementary European Search Report dated Jan. 24, 2020, issued in European Patent Application No. 17824445.5.

* cited by examiner

DEODORIZATION MODULE AND STORAGE APPARATUS COMPRISING SAME

CROSS REFERENCE TO RELATED APPLICATIONS

This application is a Continuation of International Patent Application No. PCT/KR2017/006829, filed on Jun. 28, 2017, and claims priority from and the benefit of Korean Patent Application No. 10-2016-0084771, filed on Jul. 5, 2016, each of which is incorporated by reference for all purposes as if fully set forth herein.

BACKGROUND

Field

Exemplary embodiments/implementations of the invention relate generally to a deodorization module and a storage apparatus including the same.

Discussion of the Background

A refrigerator is used to store food for a long period of time while preventing the food from going bad. Generally, the temperature of the refrigerator is regulated within a range of 0° C. to 10° C. If food is left unattended in the refrigerator for a long enough time, the food starts to decay, smells bad, and offends a user. When a food absorbs the smell of another food, it loses its unique smell and spoils.

For this reason, most refrigerators are equipped with various deodorization apparatuses for removing the smell of food itself or the odor of decaying food, preventing circulation of the odor, and providing sterilization.

Typical deodorization apparatuses use a deodorization filter in which manganese oxide (MnO2), copper oxide (CuO), an artificial enzyme catalyst, and the like are supported on a lattice of activated carbon. However, such deodorization apparatuses draw in a small amount of air per unit time and thus have low deodorization efficiency. In addition, an air passage inside the deodorizing device is narrow, causing partial loss of suctioned air. Further, the deodorization filter has a small area and thus cannot provide sufficient deodorization.

The above information disclosed in this Background section is only for understanding of the background of the inventive concepts, and, therefore, it may contain information that does not constitute prior art.

SUMMARY

It is one aspect of the inventive concepts to provide a deodorization module capable of deodorizing air in a storage chamber and a storage apparatus including the same.

It is another aspect of the inventive concepts to provide a deodorization module which draws in air and deodorizes the suctioned air, and a storage apparatus including the same.

It is a further aspect the inventive concepts to provide a deodorization module which can deodorize suctioned air without loss and exhibit improved deodorization performance using a deodorization filter having an increased area, and a storage apparatus including the same.

It is yet another aspect the inventive concepts to provide a deodorization module capable of deodorizing suctioned air without loss and a storage apparatus including the same.

In accordance with an exemplary embodiment of the invention, there is provided a deodorization module including: a housing, wherein one surface of the housing includes a curved surface; a suction hole formed through the one surface of the housing to allow air to be drawn into the housing therethrough; a fan disposed at the suction hole to draw in air; a discharge hole formed through the one surface of the housing to allow the air drawn in by the fan to be discharged from the housing therethrough; a photocatalyst filter disposed between the fan and the discharge hole and including a through-hole through which the air passes; and a light source module emitting ultraviolet (UV) light toward the photocatalyst filter.

In accordance with another exemplary embodiment, there is provided a storage apparatus including: a storage chamber having an internal space; and a deodorization module mounted on the storage chamber to deodorize air inside the storage chamber.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the scope of the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the scope of the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules, such as control boards and control units. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

In accordance with one aspect of the inventive concepts, a deodorization module includes: a housing, wherein one surface of the housing includes a curved surface; a suction hole formed through the one surface of the housing to allow air to be drawn into the housing therethrough; a fan disposed at the suction hole to draw in air; a discharge hole formed through the one surface of the housing to allow the air drawn in by the fan to be discharged from the housing therethrough; a photocatalyst filter disposed between the fan and the discharge hole and including a through-hole through which the air passes; and a light source module emitting light toward the photocatalyst filter. Here, the one surface of the housing may be entirely or partially curved. Thus, the deodorization module has a smaller volume than a deodorization module including a cuboid housing. The suction hole and the discharge hole may be formed through the one surface of the housing including the curved surface. In addition, the curved surface may be concave.

The fan may be an axial flow fan. The fan may contact the suction hole. Thus, the fan directly draws in air of outside the housing, such that a large amount of air can be drawn into the deodorization module. In addition, the air drawn in by the fan may pass through the photocatalyst filter before being discharged from the housing through the discharge hole.

The fan may be disposed in an inclined manner such that a space is formed between the fan and the suction hole. In this case, the deodorization module may further include a fan seating member disposed in an inclined manner at the suction hole and formed with a through-hole allowing air to be suctioned therethrough, wherein the fan may be seated on the fan seating member.

The air drawn in by the fan may pass through the photocatalyst filter before being discharged from the housing through the discharge hole. All side surfaces of the photocatalyst filter may tightly contact an inner surface of the housing. In this way, the entire internal space of the housing provides an air flow passage and all of the air drawn into the deodorization module passes through the photocatalyst filter, whereby efficient air deodorization can be achieved.

The deodorization module may further include a pair of filter securing members formed on respective opposite inner side surfaces of the housing and configured to receive respective opposite side surfaces of the photocatalyst filter.

The light source module may be disposed between the photocatalyst filter and the discharge hole. Alternatively, the light source module may be disposed between the fan and the photocatalyst filter.

The deodorization module may further include a pair of module securing members formed on respective opposite inner side surfaces of the housing and configured to receive respective opposite side surfaces of the light source module.

The light source module may include: a light source substrate; and a light source. The light source module may include a plurality of light sources. The light source module may further include a heat sink.

The deodorization module may further include a discharge guide formed on one inner surface of the housing between the photocatalyst filter and the discharge hole to have a predetermined height. The discharge guide may be formed between the discharge hole and an inner side surface of the housing.

The housing may further include an air suction guide formed between one surface of the fan and one inner side surface of the housing and between the other surface of the fan and the other inner side surface of the housing.

The housing may be formed of a reflective material or an inner surface of the housing may be coated with a reflective material.

The housing may further include an external guide protruding outward along around the outer side surfaces of the housing.

The housing may be divided into: a main body having an open portion and receiving the fan, the photocatalyst filter, and the light source module; and a cover covering the open portion of the main body, wherein the cover is detachably coupled to the main body.

In accordance with another aspect of the inventive concepts, a storage apparatus includes: a storage chamber having an internal space; and a deodorization module mounted on the storage chamber to deodorize air inside the storage chamber.

The storage chamber may include a groove-shaped deodorization module mount portion. The deodorization module may be inserted into the deodorization module mount portion such that the suction hole and the discharge hole of the deodorization module are exposed to the internal space of the storage chamber.

The storage chamber may be a refrigerator or a heating cabinet.

As used herein, terms such as "upper", "lower", "right", and "left" are defined with reference to the accompanying drawings. However, it should be understood that the definition is given for descriptive convenience and is not to be construed in any way as limiting the present invention.

Figure 1:
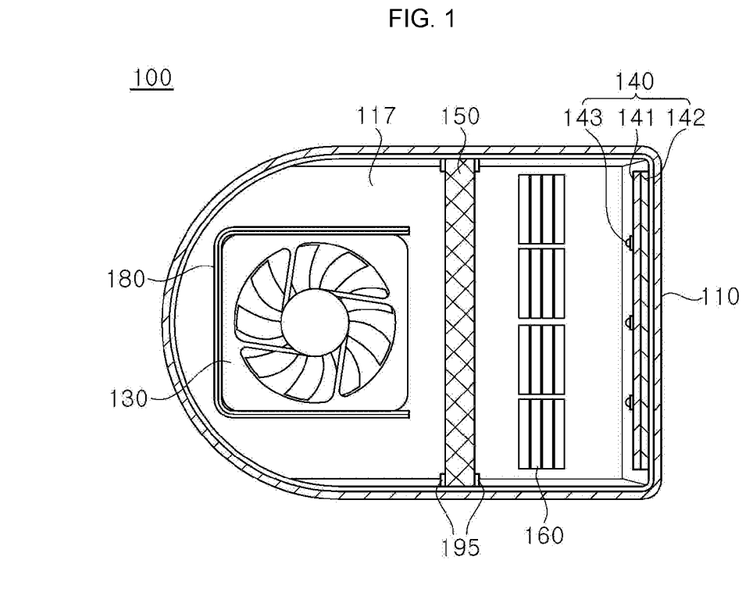
FIG. 1 is a top sectional view of a deodorization module according to a first exemplary embodiment of the inventive concepts
Figure 2:
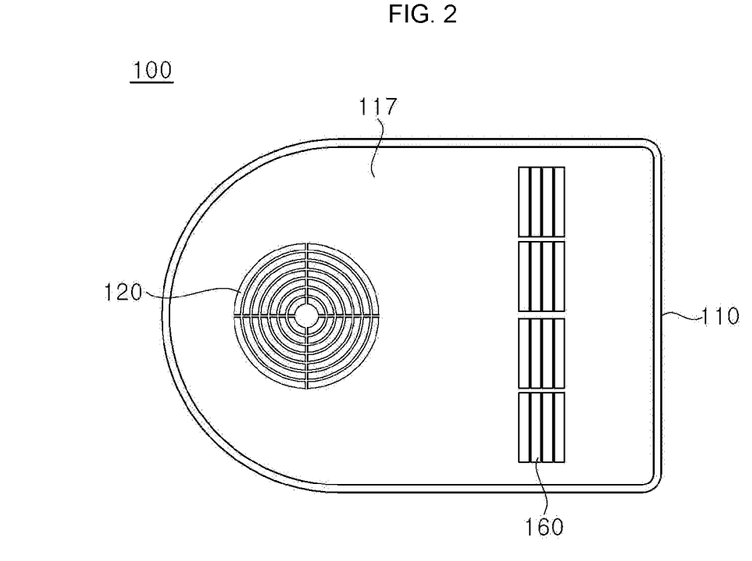
FIG. 2 is a bottom elevation view of the deodorization module according to the first exemplary embodiment.
Figure 3:
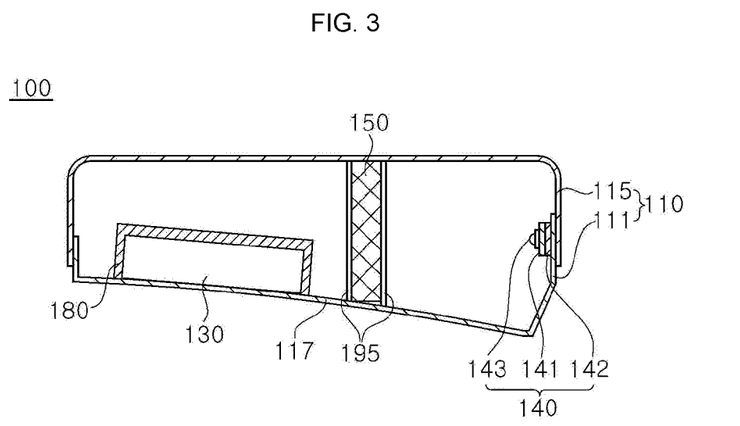
FIG. 3 is a side sectional view of the deodorization module according to the first exemplary embodiment.
Figure 4:
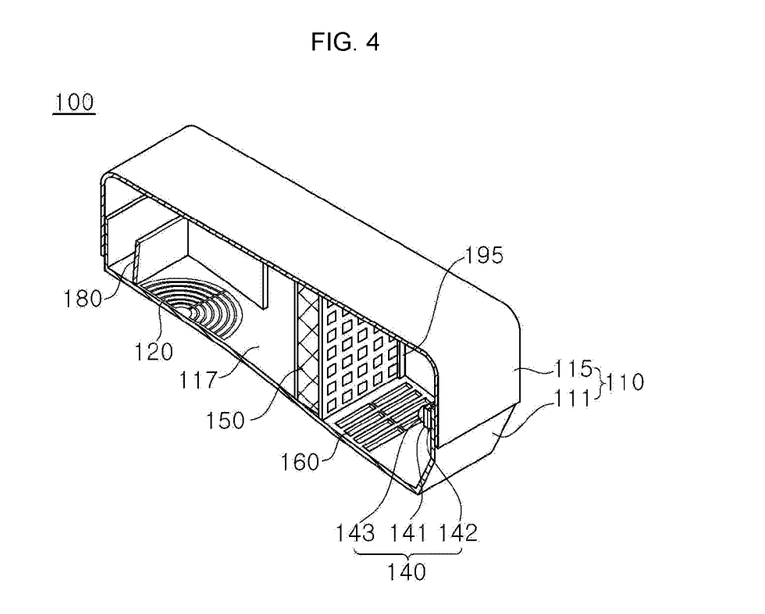
FIG. 4 is a perspective side sectional view of the deodorization module according to the first exemplary embodiment.

FIG. 1 to FIG. 4 are exemplary views of a deodorization module according to a first exemplary embodiment of the inventive concepts. FIG. 1 is a top sectional view of the deodorization module according to the first exemplary embodiment. FIG. 2 is a bottom elevation view of the deodorization module according to the first exemplary embodiment. FIG. 3 is a side sectional view of the deodorization module according to the first exemplary embodiment. FIG. 4 is a perspective side sectional view of the deodorization module according to the first exemplary embodiment.

Referring to FIG. 1 to FIG. 4, the deodorization module 100 according to the first exemplary embodiment includes a housing 110, a suction hole 120, a fan 130, a discharge hole 160, a photocatalyst filter 150, and a light source module 140.

One surface of the housing 110 is a curved surface. The curved surface is curved inwardly of the housing 110. Here, referring to FIG. 2 and FIG. 3, the one surface of the housing 110 is a bottom 117 of the housing 110.

The suction hole 120 and the discharge hole 160 are formed through the bottom 117 of the housing 110. In addition, the housing 110 receives the fan 130, the photocatalyst filter 150, and the light source module 140.

The suction hole 120 is a hole through which air is drawn into the housing 110. The suction hole 120 is formed in a region where the fan 130 is disposed.

The discharge hole 160 is a hole through which air deodorized through the photocatalyst filter 150 is discharged from the housing 110. Thus, the photocatalyst filter 150 is disposed between the suction hole 120 and the discharge hole 160.

A suction guide 180 may be formed at both sides of the suction hole 120. The suction guide 180 protrudes upward from a lower inner surface of the housing 110. In addition, the suction guide 180 is open between the fan 130 and the light source module 140. Thus, the suction guide 180 serves to guide the air drawn in by the fan 130 through the suction hole 120 to move to the light source module 140.

The fan 130 is disposed on the suction hole 120. In this exemplary embodiment, the fan 130 is an axial flow fan. The axial flow fan is a blower having a rotation axis parallel to the direction of a flow of air. The fan 130 directly draws in air outside the housing 110 through the suction hole 120 and discharges the air directly into the housing 110. In this way, the axial flow fan 130 can draw in a large amount of air at once, thereby improving deodorization efficiency.

The fan 130 may be fitted into the suction guide 180 so as to be secured in the housing 110. Alternatively, the axial flow fan 130 may be coupled to the bottom of the housing 110 using a screw. However, it should be understood that the present invention is not limited thereto and the fan 130 may be secured in the housing 110 by any suitable fastening method known in the art.

The photocatalyst filter 150 is disposed between the fan 130 and the discharge hole 160. For example, photocatalyst filter 150 may be provide in the form of a bar having a plurality of through-holes. The photocatalyst filter 150 may be a porous ceramic coated with a photocatalytic material. Alternatively, the photocatalyst filter 150 may be formed of a metal foam coated with a photocatalytic material. The metal foam may include nickel (Ni), iron (Fe), aluminum (Al), chromium (Cr), and the like. The photocatalytic material may include at least one selected from the group consisting of $TiO_2$, $ZnO$, $ZrO_2$, and $WO_3$. Alternatively, the photocatalyst filter 150 itself may contain the photocatalytic material.

The photocatalyst filter 150 may be secured in the housing 110 using a pair of filter securing members 195. The pair of filter securing members 195 protrudes inward from opposite inner side surfaces of the housing 110, respectively. In addition, each of the pair of filter securing members 195 has a vertical groove formed thereon to extend from the top to the bottom thereof. Thus, the photocatalyst filter 150 is secured in the housing 110 by inserting opposite side surfaces of the photocatalyst filter into the respective grooves of the pair of filter securing members 195. In one exemplary embodiment, the filter securing member 195 may be formed separately of the housing 110. In another exemplary embodiment, the filter securing member 195 may be integrally formed with the housing 110. In other words, the filter securing member 195 may be an integral part of the housing 110.

The photocatalyst filter 150 is disposed such that air drawn in by the fan 130 can pass through the photocatalyst filter 150. For example, opposite side surfaces of the photocatalyst filter 150 may tightly contact opposite inner side surfaces of the housing 110, respectively. In addition, an upper side surface of the photocatalyst filter 150 may tightly contact the upper inner surface of the housing 110. Further, a lower side surface of the photocatalyst filter 150 may tightly contact the lower inner surface of the housing 110. Since the all side surfaces of the photocatalyst filter 150 tightly contact the inner surfaces of the housing 110, the air drawn into the housing will necessarily pass through the photocatalyst filter 150. That is, all of the air drawn into the housing 110 is deodorized by the light source module 140 before being discharged from the housing 110.

The light source module 140 is emits light that activates the photocatalytic reaction. For example, the light source module 140 may emit ultraviolet (UV) light. The light source module 140 is disposed between the discharge hole 160 and one inner surface of the housing 110. Here, the one inner surface of the housing 110 refers to a surface which faces the photocatalyst filter 150. The light source module 140 includes a light source substrate 141, a heat sink 142, and a light source. For example, the light source may be UV light source 143.

The light source substrate 141 is electrically connected to the UV light source 143 and applies electrical signals to the UV light source 143. For example, the light source substrate 141 may be a printed circuit board or a metal printed circuit board. When the light source substrate 141 is a metal printed circuit board, the light source module 140 can have improved heat dissipation performance.

The UV light source 143 is mounted on one surface of the light source substrate 141. The UV light source 143 emits UV light toward the photocatalyst filter 150. For example, the UV light source 143 may be an LED chip. The UV light source 143 may include one or more UV light sources. When plural UV light sources 143 are mounted on the light source substrate 141, the photocatalyst filter 150 can be evenly irradiated with UV light. The number of UV light sources 143 may be adjusted, as needed.

The heat sink 142 is formed on the other surface of the light source substrate 141. The heat sink 142 may be attached to the other surface of the light source substrate 141 using a thermally conductive adhesive. The heat sink 142 is configured to dissipate heat from the UV light source 143 and the light source substrate 141. The heat sink 142 is formed of a thermally conductive material. For example, the heat sink 142 may be formed of a metal. In this exemplary embodiment, it has been described that the light source module 140 includes the heat sink 142. However, it should be understood that the present invention is not limited thereto. That is, the heat sink 142 may be omitted, as needed. In addition, the heat sink 142 may be formed of any suitable material known in the art and may be attached to the light source substrate 141 by any suitable method known in the art.

UV light emitted from the UV light source 143 reacts with the photocatalytic material of the photocatalyst filter 150 to generate hydroxyl radicals (.OH). The hydroxyl radicals decompose and remove pollutants or odorous substances. That is, air drawn in by the fan 130 is deodorized in the process of passing through the through-holes of the photocatalyst filter 150.

In FIG. 1, the light source module 140 is shown as attached to the inner surface of the housing 110. However, it should be understood that the present invention is not limited thereto and the light source module 140 may be spaced apart from the inner surface of the housing 110.

In this exemplary embodiment, the interior of the housing 110 provides a passage through which air drawn in by the fan 130 flows to the photocatalyst filter 150. In this way, the air drawn in by the fan 130 can flow to the photocatalyst filter 150 without loss. In addition, since the photocatalyst filter 150 is disposed across the entirety of the air flow passage in the housing 110, the air necessarily passes through the photocatalyst filter before being discharged to the outside. Thus, the deodorization module 100 can exhibit high air deodorization efficiency.

The housing 110 may be divided into a main body 111 and a cover 115. The main body 111 of the housing 110 is configured to receive the fan 130, the photocatalyst filter 150, and the light source module 140 and is partially open. In this exemplary embodiment, the main body 111 is open at a top thereof.

The cover 115 of the housing 110 covers an open portion of the main body 111. That is, in this exemplary embodiment, the cover 115 is disposed over the main body 111 to cover the open top of the main body 111.

The cover 115 of the housing 110 is detachably coupled to the main body 111. A coupling structure between the main body 111 and the cover 115 is not limited to the structure shown in the drawings. That is, any coupling structure may be employed so long as the housing 110 can receive the fan 130, the photocatalyst filter 150, and the light source module 140 when the cover 115 of the housing 110 is coupled to the main body 111.

The deodorization module 100 may include a control board. The control board supplies electrical power and control signals to the centrifugal fan 130 and the light source module 140. The control board may be omitted or may be disposed outside the housing 110, as needed.

Figure 5:
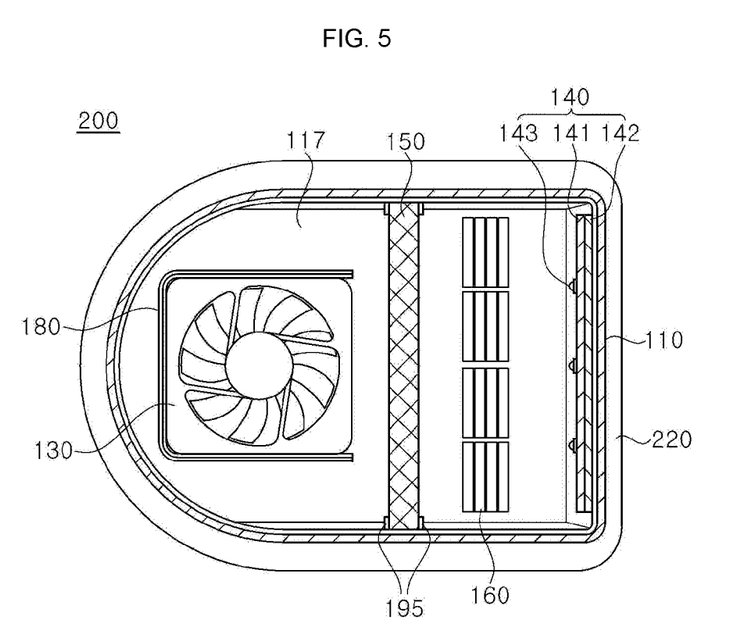
FIG. 5 is a top sectional view of a deodorization module according to a second exemplary embodiment of the inventive concepts.
Figure 6:
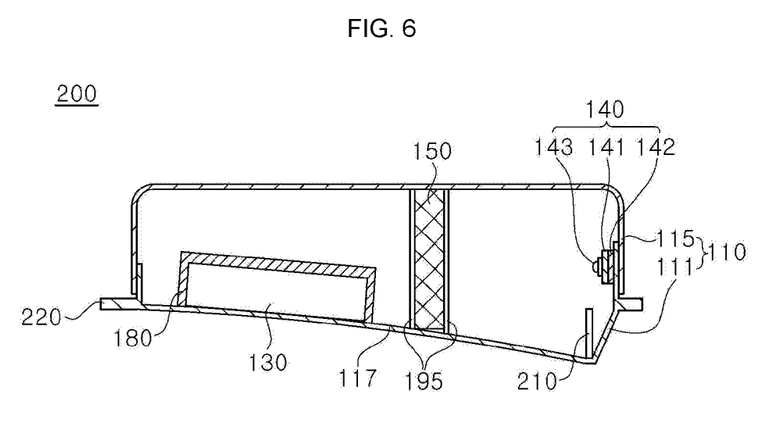
FIG. 6 is a side sectional view of the deodorization module according to the second exemplary embodiment.

FIG. 5 and FIG. 6 are exemplary views of a deodorization module according to a second exemplary embodiment of the inventive concepts. FIG. 5 is a top sectional view of the deodorization module according to the second exemplary embodiment. FIG. 6 is a side sectional view of the deodorization module according to the second exemplary embodiment.

With regard to the deodorization module 200 according to the second exemplary embodiment, detailed description of the same components as those of the deodorization module 100 according to the first exemplary embodiment (FIG. 1 to FIG. 4) will be omitted. For omitted details, refer to the description related to the deodorization module according to the first exemplary embodiment.

In this exemplary embodiment, the deodorization module further includes a bottom discharge guide 210 disposed between the light source module 140 and the discharge hole 160. The bottom discharge guide 210 is formed on the bottom of the housing 110 to have a predetermined height.

Air passing through the photocatalyst filter 150 travels along the shortest path to the discharge hole 160. Thus, most of the air will pass through a lower portion of the photocatalyst filter 150. According to the inventive concepts, the bottom discharge guide 210 formed between the photocatalyst filter 150 and the discharge hole 160 prevents a flow of the air from being concentrated in a certain area. That is, with the bottom discharge guide 210, the air can pass throughout the entire one surface of the photocatalyst filter 150, whereby the deodorization module 200 can have improved deodorization efficiency.

In this exemplary embodiment, the deodorization module further includes an external guide 220 formed on an outer surface of the housing 110. The external guide 220 protrudes outward along around the outer side surface of the housing 110. With the external guide 220, the depth to which the deodorization module 200 is inserted into a refrigerator can be adjusted when the deodorization module is mounted in the refrigerator.

Figure 7:
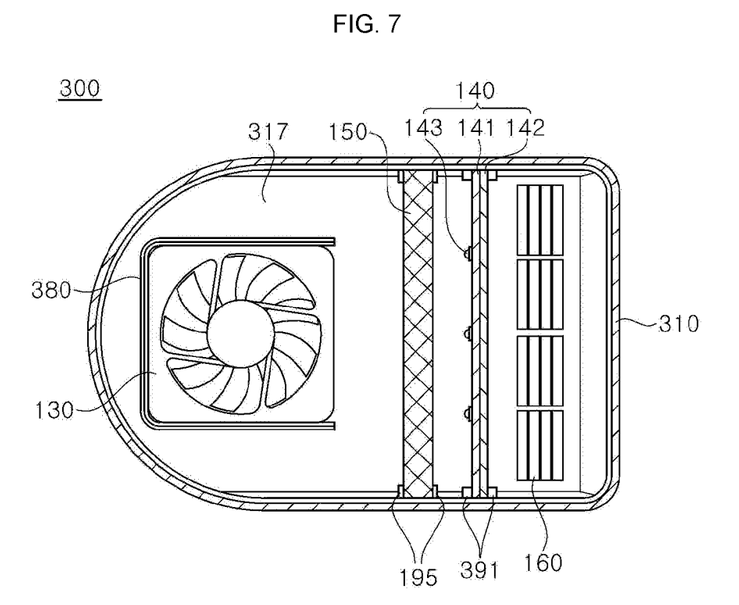
FIG. 7 is a top sectional view of a deodorization module according to a third exemplary embodiment of the inventive concepts.
Figure 8:
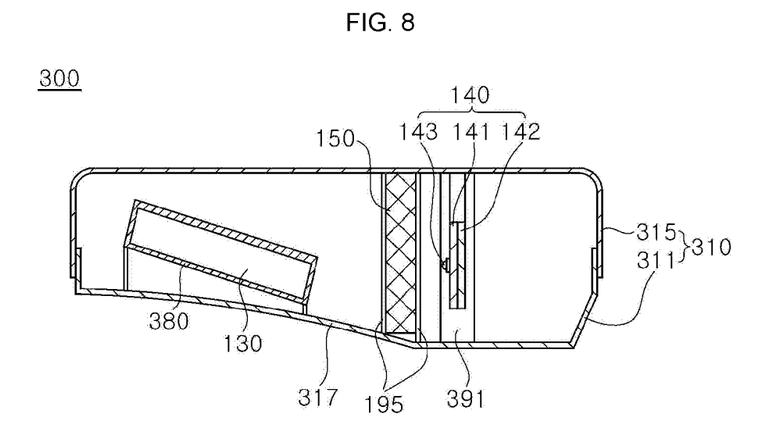
FIG. 8 is a side sectional view of the deodorization module according to the third exemplary embodiment.

FIG. 7 and FIG. 8 are exemplary views of a deodorization module according to a third exemplary embodiment of the inventive concepts. FIG. 7 is a top sectional view of the deodorization module according to the third exemplary embodiment. FIG. 8 is a side sectional view of the deodorization module according to the third exemplary embodiment.

With regard to the deodorization module 300 according to the third exemplary embodiment, detailed description of the same components as those of the deodorization modules 100, 200 according to the first to second exemplary embodiments (FIG. 1 to FIG. 6) will be omitted. For omitted details, refer to the description related to the deodorization modules according to the first to second exemplary embodiments.

In this exemplary embodiment, the deodorization module includes a housing 310 including a main body 311 and a cover 315. In addition, a bottom 317 of the housing 310 is partially curved.

The suction hole 120 is formed through a curved portion of the bottom 317 of the housing 310 and the discharge hole 160 is formed through a flat portion of the bottom of the housing. In addition, the photocatalyst filter 150 and a fan seating member 380 are disposed at the curved portion of the bottom 317 of the housing 310. Further, the light source module 140 is disposed at the flat portion of the bottom 317 of the housing 310. However, it should be understood that positions of the photocatalyst filter 150 and the light source module 140 are not limited thereto. That is, each of the photocatalyst filter 150 and the light source module 140 may be disposed at either the curved portion or the flat portion of the bottom 317 of the housing 310.

The fan seating member 380 is disposed in an inclined manner at the suction hole 120. In addition, the fan seating member 380 is formed with a through-hole allowing air to be suctioned therethrough. The fan 130 is seated on the fan seating member 380. Here, the rotation axis of the fan 130 may be perpendicular to the through-hole of the fan seating member 380.

The fan 130 is disposed in an inclined manner inside the housing 310 such that a space is formed between the fan 130 and the suction hole 120. The fan 130 draws air into the housing 310 through the suction hole 120 and the through-hole of the fan seating member 380.

The light source module 140 is disposed between the photocatalyst filter 150 and the discharge hole 160. Opposite side surfaces of the light source module 140 tightly contact opposite inner side surfaces of the housing 310, respectively. In addition, upper and lower surfaces of the light source module 140 are spaced apart from upper and lower inner surfaces of the housing 310, respectively. Spaces between the light source module 140 and the housing 310 provide an air flow passage. That is, the air deodorized through the photocatalyst filter 150 flows to the discharge hole 160 through the spaces between the light source module 140 and the housing 310.

The light source module 140 is secured to the inner side surface of the housing 310 using a pair of module securing members 391. Each of the pair of module securing members 391 has a vertical groove formed thereon to extend from the top thereof. Here, the depth of the groove may vary depending on the height at which the light source module 140 is to be positioned.

The light source module 140 is secured to the inner side surface of the housing 310 by inserting opposite side surfaces of the light source module into the respective grooves of the pair of module securing members 391. In FIG. 7, the opposite side surfaces of the light source module 140 inserted into the respective grooves of the pair of module securing members 391 refer to opposite side surfaces of the light source substrate 141 and opposite side surfaces of the heat sink 142. However, when the heat sink 142 is omitted or depending on the structure of the heat sink 142, only the light source substrate 141 may be inserted into the pair of module securing members 391.

In this exemplary embodiment, it has been described that the pair of module securing members 391 is formed separately of the housing 310. However, it should be understood that the present invention is not limited thereto and the pair of module securing members 391 may be integrally formed with the housing 310.

Figure 9:
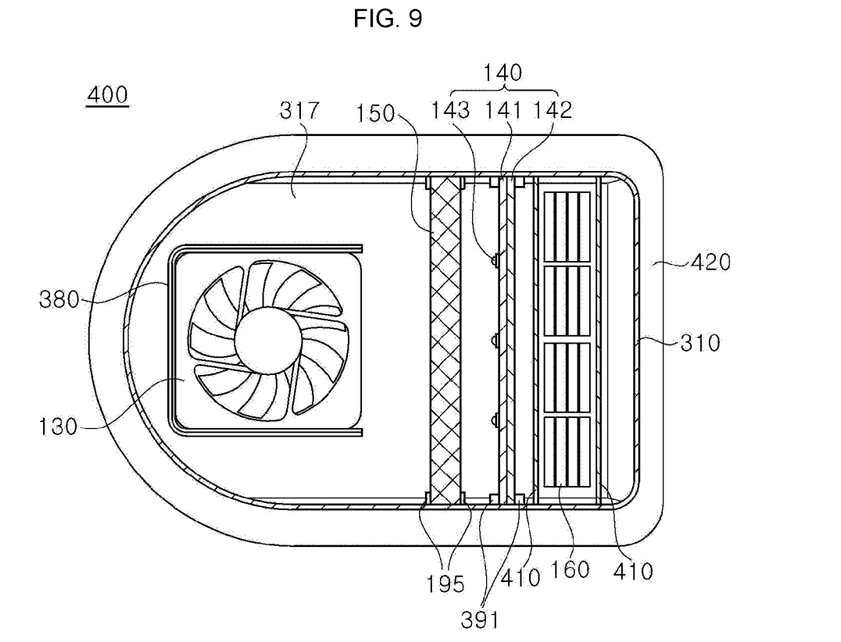
FIG. 9 is a top sectional view of a deodorization module according to a fourth exemplary embodiment of the inventive concepts.
Figure 10:
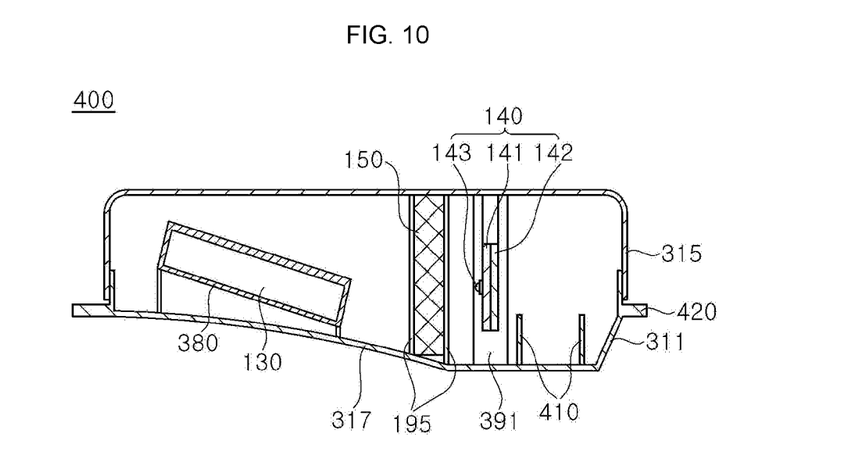
FIG. 10 is a side sectional view of the deodorization module according to the fourth exemplary embodiment.

FIG. 9 and FIG. 10 are exemplary views of a deodorization module according to a fourth exemplary embodiment of the inventive concepts. FIG. 9 is a top sectional view of the deodorization module according to the fourth exemplary embodiment. FIG. 10 is a side sectional view of the deodorization module according to the fourth exemplary embodiment.

With regard to the deodorization module 400 according to the fourth exemplary embodiment, detailed description of the same components as those of the deodorization modules 100, 200, 300 according to the first to third exemplary embodiments (FIG. 1 to FIG. 8) will be omitted. For omitted details, refer to the description related to the deodorization modules according to the first to third exemplary embodiments.

In this exemplary embodiment, the deodorization module includes a pair of bottom discharge guides 410. One of the pair of bottom discharge guides 410 is formed between the light source module 140 and the discharge hole 160. The other one of the pair of bottom discharge guides 410 is formed between the discharge hole 160 and one inner surface of the housing 310. Here, the one inner surface of the housing 310 refers to a surface which faces the photocatalyst filter 150.

The pair of bottom discharge guides 410 formed at respective opposite sides of the discharge hole 160 guides deodorized air to the discharge hole 160.

In addition, the deodorization module includes an external guide 420 formed on an outer surface of the housing 310. The external guide 420 protrudes outward along around the outer side surfaces of the housing 310. With the external guide 420, the depth to which the deodorization module 400 is inserted into a refrigerator can be adjusted when the deodorization module is mounted in the refrigerator.

The deodorization module according to the inventive concepts have been described with reference to FIG. 1 to FIG. 10. However, the inventive concepts are not limited to the positions of the light source module 140 shown in FIG. 1 to FIG. 10. The light source module 140 may be disposed at any location so long as the light source module 140 can emit UV light toward the photocatalyst filter 150.

Figure 11:
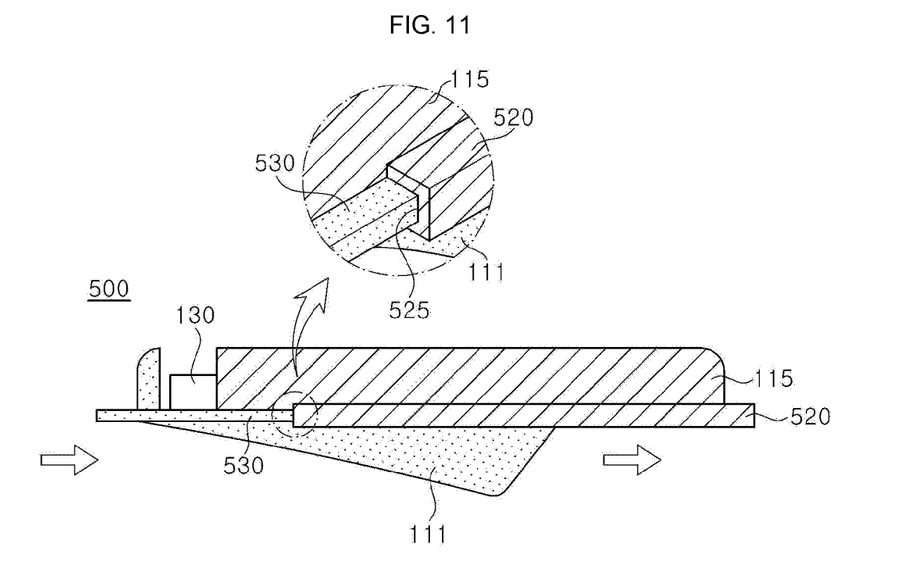
FIG. 11 is an exemplary view of a deodorization module according to a fifth exemplary embodiment of the inventive concepts.

FIG. 11 is an exemplary view of a deodorization module according to a fifth exemplary embodiment of the inventive concepts.

With regard to the deodorization module 500 according to the fifth exemplary embodiment, detailed description of the same components as those of the deodorization modules 100, 200, 300, 400 according to the first to fourth exemplary embodiments (FIG. 1 to FIG. 10) will be omitted. For omitted details, refer to the description related to the deodorization modules according to the first to fourth exemplary embodiments.

In this exemplary embodiment, the deodorization module 500 includes a first external guide 520 and a second external guide 530.

The first external guide 520 protrudes outward along around the outer side surfaces of the cover 115. Here, a portion of the outer side surfaces of the cover 115 is not formed with the first external guide 520.

The first external guide 520 has a groove 525 formed thereon. Here, the groove 525 is formed along an inner side of the first external guide 520.

The second external guide 530 protrudes outward along around the outer side surfaces of the main body 111. The second external guide 530 includes a shape corresponding in shape to the groove 525 of the first external guide 520.

For the deodorization module 500, the main body 111 is coupled to the cover 115 by inserting the second external guide 530 into the groove 525 of the first external guide 520.

Referring to FIG. 11, the first external guide 520 is continuously formed along a rear surface and portions of side surfaces of the cover 115. The second external guide 530 is continuously formed along front surface, rear surface, and side surfaces of the main body 111. The second external guide 530 is inserted into the groove 525 through one end of the first external guide 520. Then, the second external guide 530 is pushed in a direction of the rear surface of the cover. In this way, the main body 111 can be coupled to the cover 115 by pushing the second external guide 530 into the first external guide 520.

In FIG. 11, the bottom of the deodorization module is shown as partially curved. However, it should be understood that the inventive concepts are not limited thereto and the first external guide 520 and the second external guide 530 may also be applied to a deodorization module having an entirely-curved bottom.

Figure 12:
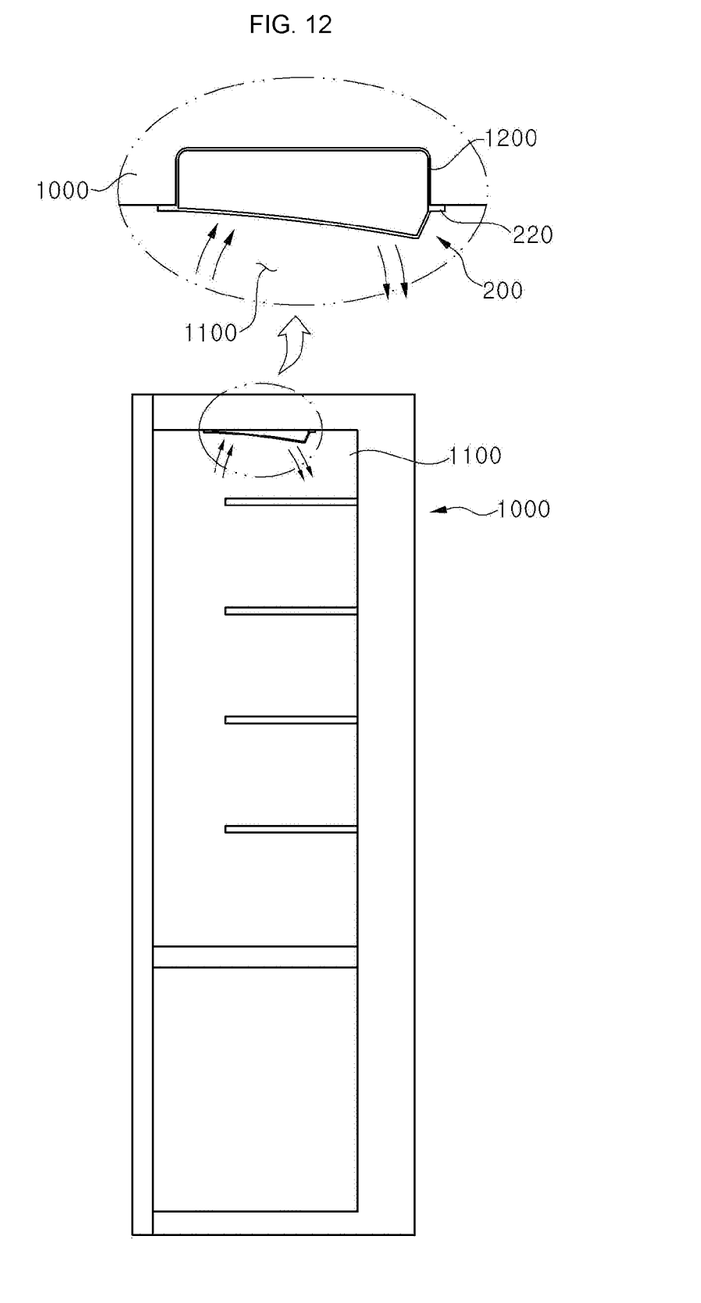
FIG. 12 is a side view of a storage apparatus according to a first exemplary embodiment of inventive concepts.

FIG. 12 is an exemplary view of a storage apparatus according to a first exemplary embodiment of the inventive concepts.

Referring to FIG. 12, the storage apparatus 1000 includes a storage chamber 1100 and a deodorization module 200.

In this exemplary embodiment, the storage apparatus 1000 is a refrigerator.

The storage chamber 1100 has an internal space. Food is stored in the internal space of the storage chamber 1100.

In addition, the storage chamber 1100 is formed with a deodorization module mount portion 1200 into which the deodorization module 200 is inserted. The deodorization module mount portion 1200 is provided in the form of a groove on an upper inner surface of the storage chamber 1100. Further, the deodorization module mount portion 1200 corresponds in shape to a portion of the deodorization module 200 which is inserted into the deodorization module mount portion.

The deodorization module 200 is the deodorization module according to the second exemplary embodiment. The deodorization module 200 is mounted on the deodorization module mount portion 1200. Here, an upper portion of the deodorization module 200 with respect to the external guide 220 is inserted into the deodorization module mount portion 1200, while a lower portion of the deodorization module 200 is located in the internal space of the storage chamber 1100. Accordingly, the suction hole and the discharge hole formed through the bottom of the deodorization module 200 are exposed to the internal space of the storage chamber 1100.

In this exemplary embodiment, the bottom of the deodorization module 200 is inclined. With the deodorization module 200 formed in this manner, available space of the storage chamber 1100 can be expanded.

When the deodorization module 200 is inserted into the deodorization module mount portion 1200, an upper surface of the external guide 220 contacts an upper inner surface of the storage chamber 1100. Here, the deodorization module 200 may be secured to the storage chamber 1100 by securing the external guide 220 to the upper inner surface of the storage chamber 1100. For example, the external guide 220 may be secured to the upper surface of the storage chamber 1100 using a screw or an adhesive.

Although the deodorization module 200 is shown as mounted on the upper inner surface of the storage chamber 1100 in FIG. 12, it should be understood that the position of the deodorization module 200 is not limited thereto. That is, the deodorization module 200 may be disposed at any location in the storage chamber 1100.

In this exemplary embodiment, the deodorization module is described as the deodorization module 200 according to the second exemplary embodiment. However, it should be understood that the present invention is not limited thereto. That is, the deodorization module mounted on the storage apparatus 1000 may be any one of the deodorization modules according to the first to fifth exemplary embodiments.

The storage apparatus 1000 includes a temperature control unit. The temperature control unit controls the temperature of the storage chamber 1100. For example, the temperature control unit may control the internal temperature of the storage chamber 1100 to be maintained within a range of 0° C. to 10° C.

In this exemplary embodiment, the storage apparatus 1000 is described as a refrigerator. However, it should be understood that the present invention is not limited thereto and the storage apparatus 1000 may be any apparatus storing food. For example, the storage apparatus 1000 may be a heating cabinet.

Figure 13:
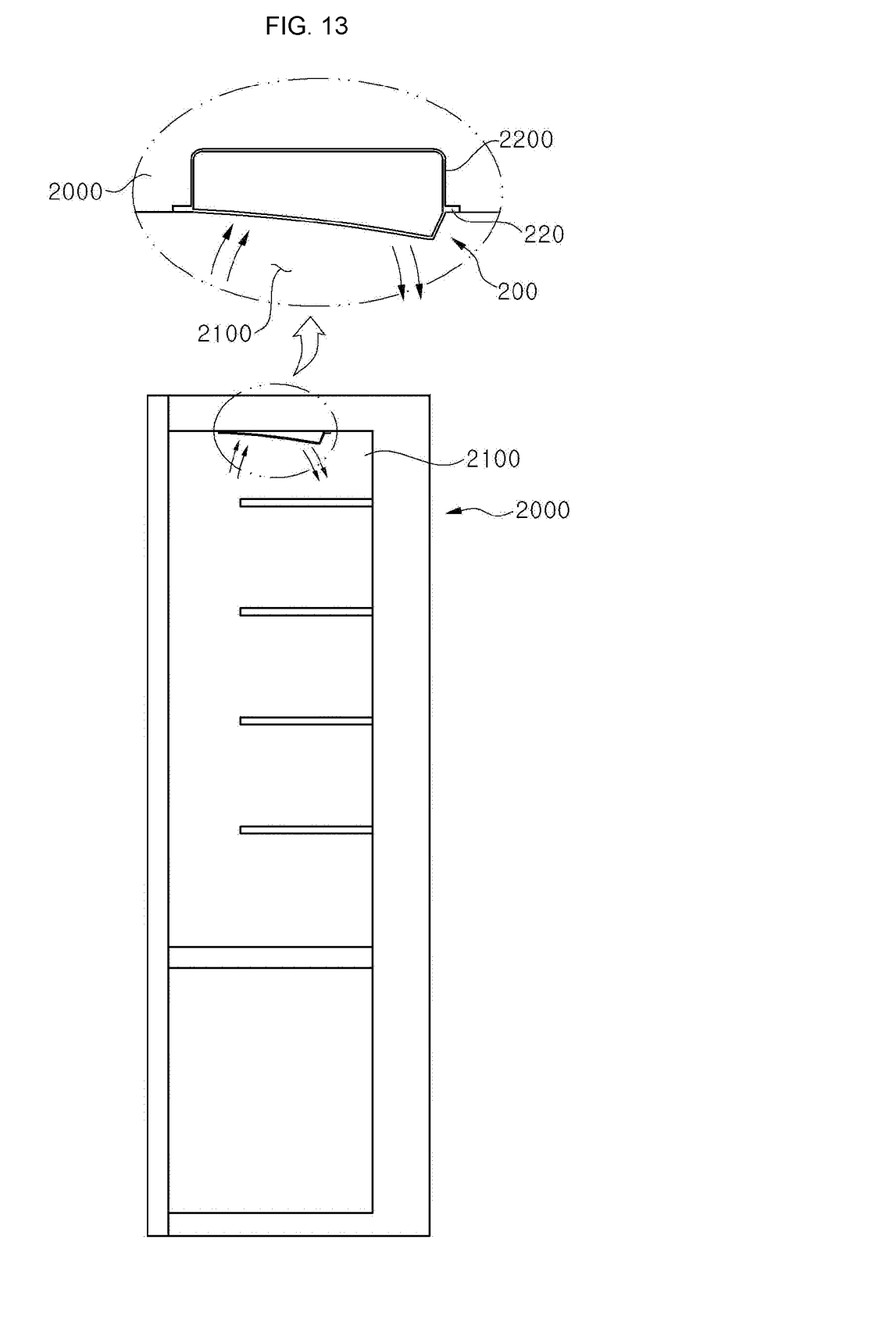
FIG. 13 is an exemplary view of the storage apparatus according to a second exemplary embodiment of the inventive concepts.

FIG. 13 is an exemplary view of a storage apparatus according to a second exemplary embodiment of the inventive concepts.

With regard to the storage apparatus 2000 according to the second exemplary embodiment, detailed description of the same components as those of the storage apparatus 1000 according to the first exemplary embodiment (FIG. 12) will be omitted. For omitted details, refer to the description related to the storage apparatus according to the first exemplary embodiment.

The deodorization module 200 is mounted on a storage chamber 2100 of a storage apparatus 2000. The deodorization module 200 is inserted into a deodorization module mount portion 2200 of the storage chamber 2100. Here, the external guide 220 of the deodorization module 200 is located inside the deodorization module mount portion 2200. That is, the deodorization module mount portion 2200 is shaped to receive the external guide 220 of the deodorization module 200.

The deodorization module 200 may be inserted into the deodorization module mount portion 2200 from the inside of the storage chamber 2100 so as to be mounted on the storage apparatus 2000. Alternatively, a space connected to the deodorization module mount portion 2200 may be formed above the storage apparatus 2000. In this case, the deodorization module 200 may be inserted into the deodorization module mount portion 2200 from above the storage apparatus 2000.

The method of mounting the deodorization module 200 on the storage apparatus 2000 has been described with reference to FIG. 12 and FIG. 13. However, it should be understood that the present invention is not limited thereto. That is, the deodorization module 200 may be mounted on the storage apparatus 2000 by any suitable method known in the art.

Although certain exemplary embodiments have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A deodorization module comprising:
a housing including a main body and a cover, wherein the main body further includes a bottom surface and side surfaces, and the bottom surface of the housing includes a curved surface that is concave when viewed from an outside of the deodorization module;
a suction hole formed through the bottom surface of the housing to allow air to be drawn into the housing therethrough;
a fan disposed at the suction hole to draw in air;
a discharge hole formed through the bottom surface of the housing to allow the air drawn in by the fan to be discharged from the housing therethrough;
a photocatalyst filter disposed between the fan and the discharge hole and comprising a first through-hole through which the air passes;
a light source module emitting light toward the photocatalyst filter for activating a photocatalytic reaction; and
a fan seating member disposed in an inclined manner at the suction hole and formed with a second through-hole allowing air to be drawn therethrough,
wherein the main body comprises an open portion and is configured to receive the fan, the photocatalyst filter, and the light source module,
wherein the cover is configured to cover the open portion of the main body, the cover being detachably coupled to the main body,
wherein the fan is seated on the fan seating member,
wherein the suction hole and the discharge hole are formed through the bottom surface of the housing comprising the curved surface,
wherein the air drawn in by the fan passes through the photocatalyst filter before being discharged from the housing through the discharge hole, and
wherein the bottom surface of the housing is entirely curved.

2. The deodorization module according to claim 1, wherein the fan contacts the suction hole.

3. The deodorization module according to claim 1, wherein the fan is disposed in an inclined manner such that a space is formed between the fan and the suction hole.

4. The deodorization module according to claim 1, wherein all side surfaces of the photocatalyst filter contact inner surfaces of the housing.

5. The deodorization module according to claim 1, further comprising:

a pair of filter securing members formed on respective opposite inner side surfaces of the housing and configured to receive respective opposite side surfaces of the photocatalyst filter.

6. The deodorization module according to claim 1, wherein the light source module is disposed between the photocatalyst filter and the discharge hole.

7. The deodorization module according to claim 1, further comprising:
a pair of module securing members formed on respective opposite inner side surfaces of the housing and configured to receive respective opposite side surfaces of the light source module.

8. The deodorization module according to claim 1, wherein the light source module comprises:
a light source substrate; and
a light source.

9. The deodorization module according to claim 8, wherein the light source module further comprises a heat sink.

10. The deodorization module according to claim 1, further comprising:
a discharge guide disposed on one inner surface of the housing between the photocatalyst filter and the discharge hole to have a predetermined height.

11. The deodorization module according to claim 10, wherein the discharge guide is disposed between the discharge hole and an inner side surface of the housing.

12. The deodorization module according to claim 1, wherein the housing further comprises an air suction guide disposed between a first surface of the fan and a first inner side surface of the housing and between a second surface of the fan and a second inner side surface of the housing.

13. The deodorization module according to claim 1, wherein the housing further comprises an external guide protruding outward from outer sides of the side surfaces of the housing.

14. A storage apparatus comprising:
a storage chamber having an internal space; and
a deodorization module mounted in the storage chamber to deodorize air inside the storage chamber,
wherein the deodorization module comprises:
a housing including a main body and a cover, wherein the main body further includes a bottom surface and side surfaces, and the bottom surface of the housing includes a curved surface that is concave when viewed from an outside of the deodorization module;
a suction hole formed through the bottom surface of the housing to allow air to be drawn into the housing therethrough;
a fan disposed at the suction hole to draw in air;
a discharge hole formed through the bottom surface of the housing to allow the air drawn in by the fan to be discharged from the housing therethrough;
a photocatalyst filter disposed between the fan and the discharge hole and comprising a first through-hole through which the air passes;
a light source module emitting light toward the photocatalyst filter for activating a photocatalytic reaction; and
a fan seating member disposed in an inclined manner at the suction hole and formed with a second through-hole allowing air to be drawn therethrough,
wherein the main body includes an open portion and receiving the fan, the photocatalyst filter, and the light source module,
wherein the cover covers the open portion of the main body, the cover being detachably coupled to the main body,
wherein the fan is seated on the fan seating member,
wherein the suction hole and the discharge hole are formed through the bottom surface of the housing comprising the curved surface,
wherein the air drawn in by the fan passes through the photocatalyst filter before being discharged from the housing through the discharge hole, and
wherein the bottom surface of the housing is entirely curved.

15. The storage apparatus according to claim 14, wherein the storage chamber comprises a groove-shaped deodorization module mount portion, and the deodorization module is inserted into the deodorization module mount portion such that the suction hole and the discharge hole of the deodorization module are exposed to the internal space of the storage chamber.

16. The storage apparatus according to claim 14, wherein the storage chamber is a refrigerator or a heating cabinet.

* * * * *